(12) United States Patent
Mittelstaedt

(10) Patent No.: US 6,406,428 B1
(45) Date of Patent: Jun. 18, 2002

(54) ULTRASOUND LENTICULAR IMAGE PRODUCT

(75) Inventor: Brian E. Mittelstaedt, West Henrietta, NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 09/461,963

(22) Filed: Dec. 15, 1999

(51) Int. Cl.[7] .................................................. A61B 8/00

(52) U.S. Cl. ...................................................... 600/437

(58) Field of Search ................................ 600/437, 443, 600/447; 378/41, 163

(56) References Cited

U.S. PATENT DOCUMENTS

| | | | | | |
|---|---|---|---|---|---|
| 3,783,282 | A | * | 1/1974 | Hoppenstein | ................ 250/313 |
| 5,207,728 | A | * | 5/1993 | Fogarty et al. | ................ 446/98 |
| 5,625,435 | A | * | 4/1997 | Lo et al. | ........................ 355/22 |
| 6,061,424 | A | * | 5/2000 | Hoppenstein et al. | ......... 378/41 |
| 6,106,463 | A | * | 8/2000 | Wilk | ........................... 600/437 |

* cited by examiner

*Primary Examiner*—Francis J. Jaworski
(74) *Attorney, Agent, or Firm*—William F. Noval

(57) ABSTRACT

An ultrasound lenticular image product comprising: a lenticular lens element; and a composite image associated with the lenticular lens element. The composite image presents a sequence of ultrasound images of a subject of interest internal to a living being, such as the motion of a fetus carried in the womb of a pregnant woman.

8 Claims, 2 Drawing Sheets

ULTRASOUND LENTICULAR IMAGE PRODUCT

FIELD OF THE INVENTION

The invention relates generally to the field of lenticular devices for the display of motion sequences, and in particular to a system and associated method for capturing and displaying a stream of data from an ultrasound scan by means of an ultra sound lenticular image product. More specifically, the invention relates to a system and method for displaying fetal ultrasound data.

BACKGROUND OF THE INVENTION

The use of ultrasound has become commonplace in the field of medical diagnostic imaging, such as in echocardiography and fetal ultrasonography. Statistically, over half of all pregnant women in the U. S. have at least one ultrasound examination prior to delivery. Currently, the market for medical ultrasound diagnostic equipment is substantial and rising.

Ultrasound is a non-invasive technique, which when properly used, causes no damage to the subject. Ultrasound imaging is based on the fact that the internal structures of the human body vary in density and composition leading to different acoustical impedances. By placing an acoustic transmitter in contact with a subject's body, acoustics waves are transmitted through the tissues. When the acoustic waves encounter an interface between two bodies of differing acoustic impedance, a portion of those waves is reflected back to an acoustic receiver, normally held in close proximity to the transmitter. The acoustic receiver converts the reflected ultrasound waves back into an electrical signal for subsequent signal processing. The reflected ultrasound signal is then used to construct an image of the reflecting structure (e.g., heart or fetus). The two dimensional image so formed is displayed on an electronic display (CRT) for evaluation by an ultrasound technician or other medical professional.

The fetal ultrasound, aside from its importance in evaluating the health of the fetus, marks an important step in the child-parent relationship. It is the first visual confirmation of the growing child within the mother. For the father, who has not had the physical changes the mother has experienced, it is the first tangible evidence of the reality of the child. In the early uses of ultrasound for fetal monitoring, the only image available to the parent(s) was the transitory image of the CRT. In time, hardcopy output was added, mainly as a recording medium for the health professional. It soon became evident that this hardcopy image was of value to the parent also. The hardcopy image was (and is) used widely by the parents to share with family and friends. The fetal ultrasound image though, represents a snapshot of a complex time-based signal in a background of noise. As such, it is often much less interpretable, and therefore, much less pleasing than the real-time scan. Recently, to overcome this problem, the medical diagnostic imaging industry has added the capability of recording the ultrasound scan to video tape. Similar to the advent of hardcopy in ultrasound, it is now quite common for parents to receive a video tape recording of the ultrasound scan of the fetus. The quality of the experience is greatly enhanced because of the ability to mentally integrate the structures of fetus revealed over time in the video. Lost from the experience though, is the ability of parents to share the experience conveniently with family and friends. There is thus a need for an ultrasound image product which is portable and which can display a motion sequence.

SUMMARY OF THE INVENTION

The present invention is directed to overcoming one or more of the problems set forth above. Briefly summarized, according to one aspect of the present invention, there is provided an ultrasound lenticular image product comprising a lenticular lens element, and a composite image associated with the lenticular lens element, wherein the composite image presents a sequence of ultrasound images of a subject of interest internal to a living being, such as the motion of a fetus carried in the womb of a pregnant woman;

According to another aspect of the present invention there is provided a method of producing such an ultrasound lenticular product.

These and other aspects, objects, features, and advantages of the present invention will be more clearly understood and appreciated from a review of the following detailed description of the preferred embodiments and appended claims, and by reference to the accompanying drawings.

ADVANTAGEOUS EFFECT OF THE INVENTION

The present invention has the following advantages.

1. A fetal ultrasound motion sequence can be shared easily with family and friends.
2. An ultrasound lenticular image product is provided that allows selection of the fetal motion sequence.

BRIEF DESCRIPTION OF THE DRAWINGS

To facilitate understanding, identical reference numerals have been used, where possible, to designate identical elements that are common to the figures.

DETAILED DESCRIPTION OF THE INVENTION

According to the present invention, ultrasound images of a subject of interest internal to a living being, such as a fetus carried in a pregnant woman's womb, are produced on a lenticular image product which allows depth or motion viewing of the subject. Although the following description is specific to ultrasound images, it will be understood that other diagnostic imaging techniques (e.g., CT, MRI, PET, NMR, etc.) may be used. Moreover, although the specific subject described is a human fetus, it will be understood that ultrasonic images of any other subject internal to the human body, such as the heart, may be used. Ultrasonic images of living beings, other than humans can also be used, such as, ultrasonic images of subjects of interest of animals (e.g., pets).

In general, ultrasonic scanning is a diagnostic technique in which very high frequency sound waves are passed into the human body. The reflected echoes are detected and analyzed to build a picture on an electronic display (monitor) of the internal organs or of a fetus in the uterus. Ultrasound waves are emitted by a transducer, which is placed on the skin over the part of the body to be viewed.

The waves used have frequencies in the range of 1 to 10 megahertz. The waves are focused into a fine parallel beam which passes through a slice of the body. Some of the waves are reflected at tissue boundaries, so a series of echoes are returned. The transducer converts the reflected waves into electrical signals which are processed and displayed on a monitor to give a two-dimensional image of the scanned body slice. By moving the transducer, different slices through the body can be seen. The fetus can also be scanned internally through the use of a transvaginal ultrasonic scan.

Figure 1:
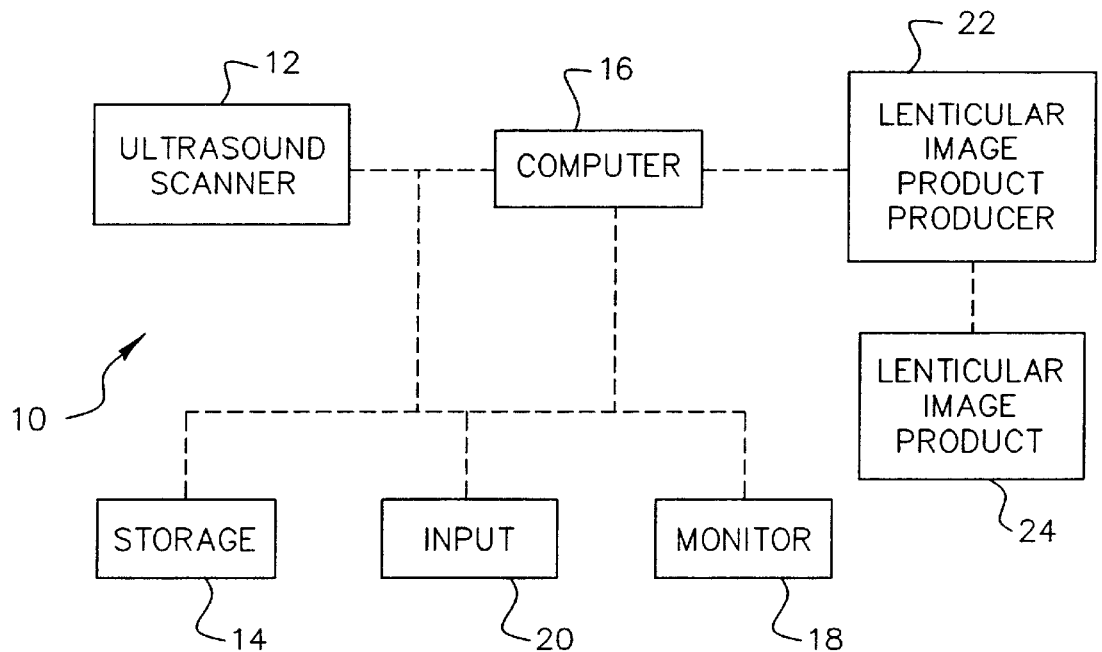
FIG. 1 is a block diagram of apparatus incorporating the present invention.

Referring now to FIG. 1, there is shown a system incorporating the present invention. As shown, system 10 includes an ultrasound scanner 12 which is used to ultrasonically scan the fetus carried in the womb of a pregnant woman. The fetal ultrasonic images are stored in storage 14, which can be part of computer 16. Computer 16 processes the fetal ultrasonic images and displays them on monitor 18. A preferred series of fetal ultrasonic images are selected by an operator through input 20. The selected fetal ultrasonic images are presented on an ultrasound lenticular image product 24 by lenticular image product producer 22.

Ultrasound scanner 12 can be any such device that is used externally or internally of the human body to produce a series of ultrasonic images of a subject of interest within the human body. The ultrasonic images are stored in storage (magnetic, optical, solid state), (1) that can be part of the ultrasound scanner equipment; (2) that is part of a computer 16 associated with the scanner 12 or at remote location, reached through a local area network, through an intranet, or through the internet or other wide area network; (3) that is transportable storage, such as, magnetic or optical disk (CD, DVD), or optical or magnetic tape (VHS, BETA). Input 20 can be any user controlled device such as a mouse, a keyboard, a touch screen, a writing tablet, etc. Monitor 18 can be any electronic display including a CRT monitor, an LCD display, etc.

Computer 16 can be used for several functions. Images can be zoomed, rotated or cropped or enhanced using image processing techniques. Through the input 18, the user can display the sequence of ultrasonic images stored in storage 14, and select the images which will be presented on the lenticular image product. The selected images can be further processed. Data relating to the baby and scan can be generated for presentation on the product (e.g., date of scan, baby's name, graphics-stork, greetings, etc.). The computer can also be used to generate the composite image to be used by producer 22. The composite image is formed by decomposing each selected ultrasonic image into a series of slices equal to the number of viewable lenticules in the lenticular image product 24. Associated with each lenticule is a set of image slices, one slice for each selected image. As an example, if there are 24 selected images, each set includes 24 image slices. The composite image can also be formed in producer 22, in which case, the whole images would be transmitted by computer 16 to producer 22.

The ultrasonic lenticular image product 24 can be produced using several techniques. Once the composite image has been formed, it can be scanned onto photosensitive media (film, paper) by laser or CRT scanning. The media is developed and combined with a lenticular sheet. The composite image can also be scanned directly onto a lenticular sheet having a photosensitive layer. The exposed layer is developed to produce the lenticular product. The composite image can be printed onto a lenticular sheet using well known printing techniques, such as, ink jet, thermal dye transfer, etc. Producer 22 can therefore include several components, printer, lenticular product assembler, lenticular product cutting and finishing, etc., depending on the production technique used.

Figure 2:
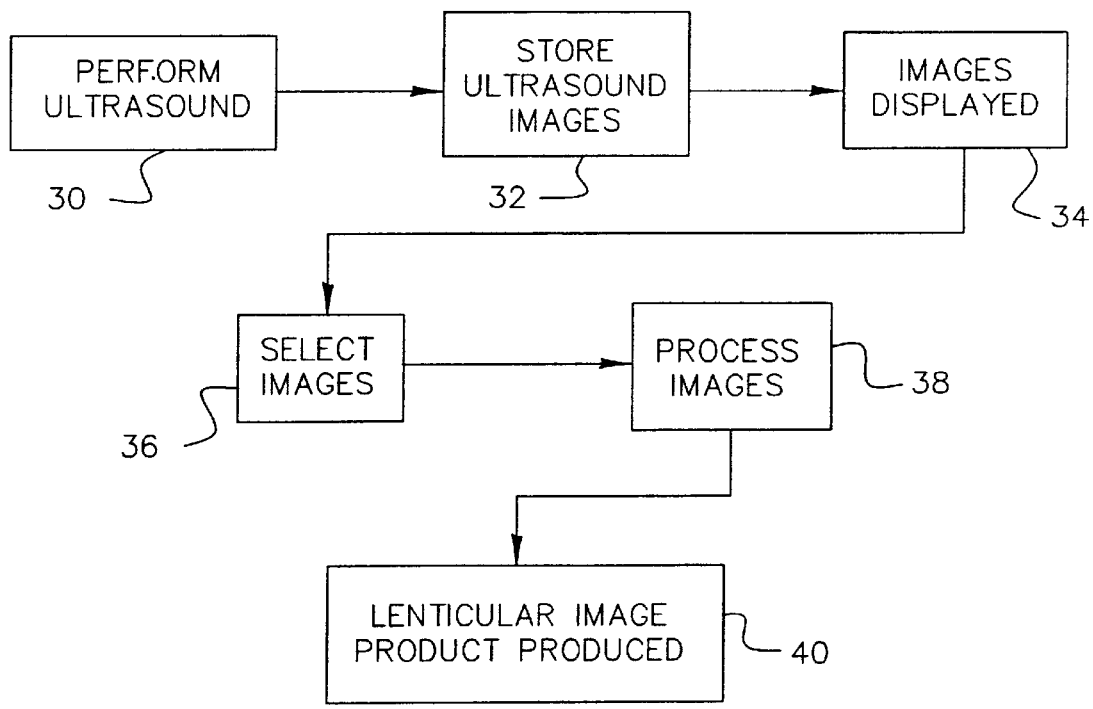
FIG. 2 is a flow diagram of the method of the present invention.

A preferred embodiment of the invention involves the isolation of the salient motion sequence by the ultrasound technician in cooperation with the fetal parent(s) and production of the lenticular image product at the time of the fetal ultrasound. As shown in FIG. 2, in this application, the ultrasound scan is performed on a pregnant woman (Box 30) and the fetal ultrasound images are stored in a video buffer (Box 32) for review by the ultrasound technician and fetal parent(s). The video buffer is capable of holding an amount of ultrasound scan data in excess of that needed to form the final image product. The stored sequence of images is displayed on a monitor (Box 34). From the buffered ultrasound scan data, a finite sequence of frames of duration between 1 and 5 seconds is selected (Box 36). The identification of the start and end points of the selected video sequence is followed by a temporal resampling (Box 38) to yield the correct number of lenticular images from the 30 frame per second video stream. For example, if 4 seconds of video at 30 frames per second have been selected (240 frames in total), and the lenticular image product presents 24 images per lenticule, then 1 in every 10 images are sampled for inclusion in the composite lenticular image. The images can be processed in other ways, such as tonal enhancement, edge sharpening, etc. The lenticular image product is then produced using the fetal composite image. It will be appreciated that the method described is applicable to other ultrasound lenticular image products.

Figure 3:
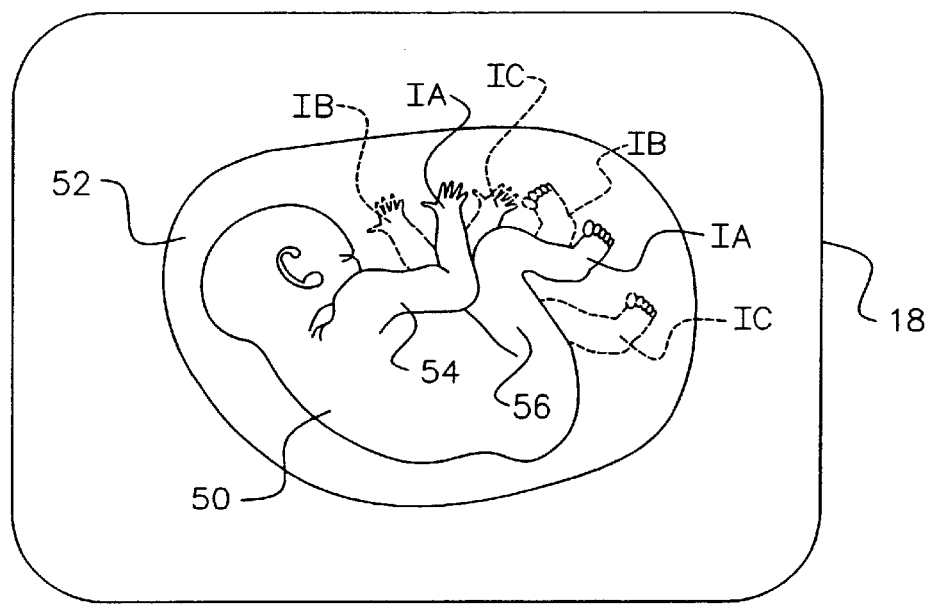
FIG. 3 is a diagrammatic view of a sequence of fetal ultrasonogram images selected for inclusion in a lenticular image product.
Figure 4:
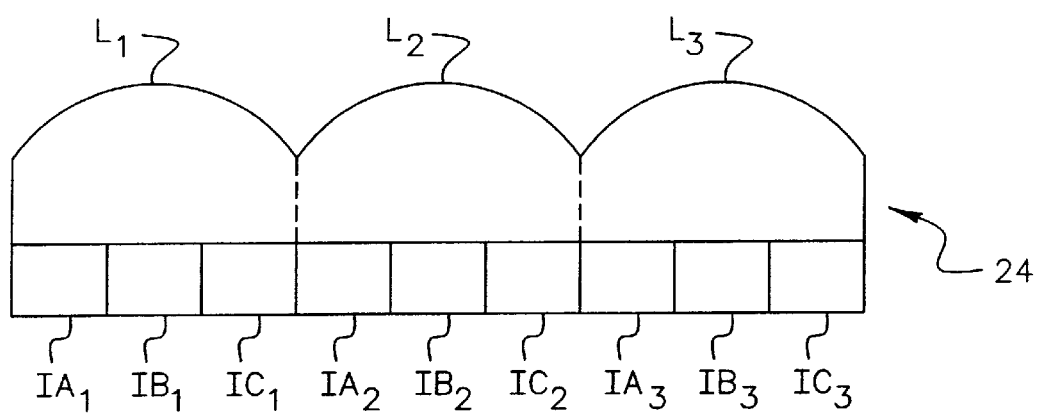
FIG. 4 is a diagrammatic view of a lenticular image product according to the present invention.

FIGS. 3 and 4 illustrate the fetal ultrasound lenticular product and method of the present invention. As shown in FIG. 3, the ultrasound image of fetus 50 in womb 52 is shown on monitor 18. Image IA shows extremities 54 and 56 in solid lines. Image IB shows extremities 54, 56 in dashed lines moved to the left of the image IA position. Image IC shows extremities 54, 56 moved to the right of the image IA position. This motion is presented on lenticular image product 24 which includes image layer 60 and lenticular lens 62 having lenticules L1, L2, L3 with cylindrical lenses. Images IA, IB, and IC are decomposed into strips respectively IA1, IA2, IA3, IB1, IB2, IB3, and IC1, IC2, IC3. Each lenticule has a set of 3 image strips associated with it, one strip from each fetal ultrasound image. Thus, lenticule L1 has image strips IA1, IB1, IC1, associated with it, lenticule L2 has image strips IA2, IB2, IC2, associated with it, and lenticule L3 has image strips IA3, IB3, IC3, associated with it. By tilting lenticular image product 22 about an axis parallel to the longitudinal axis of lenticule L2, movement of the fetus's extremities can be observed.

The invention has been described with reference to a preferred embodiment; however, it will be appreciated that variations and modifications can be effected by a person of ordinary skill in the art without departing from the scope of the invention.

PARTS LISTS 10 system
12 ultrasound scanner
14 storage
16 computer
18 monitor
20 input
22 lenticular image product producer
24 lenticular image product
30–40 boxes
50 fetus 52 womb
54, 56 extremities
60 image layer
62 lenticular lens

What is claimed is:

1. An ultrasound lenticular image product comprising:
   a lenticular lens element; and
   a permanent composite image associated with said lenticular lens element, said composite image presenting a sequence of ultrasound images of a subject of interest internal to a living being.

2. The ultrasound lenticular image product of claim 1 wherein said composite image presents a sequence of ultrasound images of a fetus carried in the womb of a pregnant woman.

3. The ultrasound lenticular image product of claim 1 wherein said lenticular lens element includes an array of parallel lenticules having cylindrical lenses.

4. The ultrasound lenticular image product of claim 1 wherein said composite image represents a sequence of ultrasound images of a human heart.

5. A method for producing a directly viewable fetal ultrasound motion card comprising:
   scanning a fetus and providing a plurality of images that capture movements of the fetus;
   selecting a number of the images that sequentially represent the desired movements of the fetus;
   slicing each of the selected number of images into strips; and
   producing a card having a transparent layer formed as a plurality of adjacent lenticular lenses and a layer of strips, one strip from each of the selected number of images being positioned under each of the lenses forming the transparent layer such that viewing of the images through the transparent layer as the card is tilted results in viewing motion of the fetal image.

6. A method for producing an ultrasound lenticular image product comprising:
   scanning a living being with an ultrasound scanner to produce a sequence of ultrasound images of a subject of interest internal to said living being;
   processing said sequence of ultrasound images by acquiring, storing and displaying said sequence of ultrasound images;
   selecting a set of said ultrasound images; and
   producing an ultrasound image product from said selected set of ultrasound images said product having a permanent set of said images.

7. The method of claim 6 wherein said scanning includes scanning a pregnant woman with said ultrasound scanner to produce a sequence of fetal ultrasound images of a fetus carried in the woman's womb.

8. The method of claim 7 wherein said sequence of fetal ultrasound images includes fetal motion and wherein said selected set of ultrasound images is used to produce an ultrasound lenticular image product presenting said fetal motion upon relative motion between said product and a viewer of said product.

* * * * *